United States Patent
Hong et al.

(10) Patent No.: US 6,358,897 B1
(45) Date of Patent: Mar. 19, 2002

(54) ALKYL TRYPSIN COMPOSITIONS AND METHODS OF USE IN CONTACT LENS CLEANING AND DISINFECTING SYSTEMS

(75) Inventors: Bor-Shyue Hong; Bahram Asgharian; Ronald P. Quintana, all of Arlington, TX (US)

(73) Assignee: Alcon Laboratories, Inc., Fort Worth, TX (US)

( * ) Notice: Subject to any disclaimer, the term of this patent is extended or adjusted under 35 U.S.C. 154(b) by 0 days.

(21) Appl. No.: 09/144,826

(22) Filed: Sep. 1, 1998

Related U.S. Application Data

(63) Continuation-in-part of application No. PCT/US96/09689, filed on Jun. 7, 1996.

(51) Int. Cl.[7] .............................. A61L 2/16; A61L 2/18; C12N 9/76
(52) U.S. Cl. .................. 510/112; 510/114; 510/370; 510/374; 510/382; 510/383; 510/392; 510/393; 510/405; 510/420; 510/421; 510/465; 510/530; 134/42
(58) Field of Search .................... 510/112, 114, 510/370, 374, 382, 383, 392, 393, 405, 420, 421, 465, 530; 134/42

(56) References Cited

U.S. PATENT DOCUMENTS

| | | | |
|---|---|---|---|
| Re. 32,672 | 5/1988 | Huth et al. | 252/95 |
| 3,910,296 | 10/1975 | Karageozian et al. | 134/2 |
| 4,407,791 | 10/1983 | Stark | 424/80 |
| 4,525,346 | 6/1985 | Stark | 424/80 |
| 4,614,549 | 9/1986 | Ogunbiyi et al. | 134/19 |
| 4,758,595 | 7/1988 | Ogunbiyi et al. | 514/635 |
| 4,836,986 | 6/1989 | Ogunbiyi et al. | 422/28 |
| 5,096,607 | 3/1992 | Mowrey-McKee et al. | 252/106 |
| 5,281,277 * | 1/1994 | Nakagawa et al. | 134/18 |
| 5,314,823 * | 5/1994 | Nakagawa | 435/264 |

(List continued on next page.)

FOREIGN PATENT DOCUMENTS

| | | |
|---|---|---|
| 1 150 907 | 8/1983 | (CA) . |
| 0 456 467 | 11/1991 | (EP) . |
| 57-24526 | 5/1982 | (JP) . |
| 89-180515 | 7/1989 | (JP) . |
| 92-143718 | 5/1992 | (JP) . |
| 92-243215 | 8/1992 | (JP) . |
| 92-370197 | 12/1992 | (JP) . |
| WO 98/25650 | 6/1998 | (WO) . |

OTHER PUBLICATIONS

Rice et al; Stabilization of Bovine Trypsin by Reductive Methylation, Biochimica et Biophysica Acta, vol. 492, pp. 316–321, 1977.*

Lo, J.; Silverman, H.; and Korb, D.; "Studies on cleaning solutions for contact lenses", *Journal of the American Optometric Association*, vol. 40, pp. 1106–1109 (1969). Nov.

Means, GE and Feeney, RE. Reduction alkylation of amino groups in proteins, *Biochemistry*, vol. 7, pp. 2192–2201 (1968) Jun.

Rice, RH, Means, GE and Brown, WD. Stabilization of bovine trypsin by reductive methylation, *Biochimica et Biophysica Acta*, vol. 492, pp. 316–321 (1977) No Month given.

Promega Corporation, "Sequencing Grade Modified Trypsin," 1996 Catalog Biological Research Products, p. 254 No Month Given.

*Primary Examiner*—Yogendra Gupta
*Assistant Examiner*—Brian P. Mruk
(74) *Attorney, Agent, or Firm*—Michael C. Mayo

(57) ABSTRACT

Improved stability, liquid enzyme compositions containing an alkylated trypsin and methods involving the combined use of these compositions with an aqueous composition are disclosed for the cleaning or simultaneous cleaning and disinfecting of contact lens. Methods for a daily use regimen are also disclosed.

24 Claims, 1 Drawing Sheet

Comparison of the Proteolytic Stability of Me-trypsin, Trypsin and Pancreatin in a Disinfecting Solution at 30°C

U.S. PATENT DOCUMENTS

| | | | |
|---|---|---|---|
| 5,576,278 | 11/1996 | Van Duzee et al. | 510/114 |
| 5,604,190 | 2/1997 | Chowhan et al. | 510/114 |
| 5,605,661 | 2/1997 | Asgharian et al. | 422/28 |
| 5,672,213 | 9/1997 | Asgharian et al. | 134/42 |
| 5,718,895 | 2/1998 | Asgharian et al. | 424/94.1 |
| 5,723,421 | 3/1998 | Chowhan et al. | 510/114 |
| 5,746,838 * | 5/1998 | Huth | 134/27 |

* cited by examiner

ALKYL TRYPSIN COMPOSITIONS AND METHODS OF USE IN CONTACT LENS CLEANING AND DISINFECTING SYSTEMS

This application is a continuation-in-part of patent application Ser. No. PCT/US96/09689, filed Jun. 7, 1996; which claims priority to U.S. patent application Ser. No. 08/544,753, filed Oct. 18, 1995, now U.S. Pat. No. 5,723,421 and U.S. patent application Ser. No. 08/477,001, filed Jun. 7, 1995, now U.S. Pat. No. 5,604,190.

BACKGROUND OF THE INVENTION

The present invention relates to the field of contact lens cleaning and disinfecting. In particular, this invention relates to concentrated or multi-purpose compositions containing alkyl trypsin and methods of use in cleaning human-worn contact lenses. The invention also relates to methods of simultaneously cleaning and disinfecting contact lenses by combining the concentrated alkyl trypsin compositions of the present invention with an aqueous composition comprising a disinfecting agent.

Various compositions and methods for cleaning contact lenses have been described in the patent and scientific literature. Some of these methods have employed compositions containing surfactants or enzymes to facilitate the cleaning of lenses. The first discussion of the use of proteolytic enzymes to clean contact lenses was in an article by Lo, et al. in the *Journal of The American Optometric Association*, volume 40, pages 1106–1109 (1969). Methods of removing protein deposits from contact lenses by means of proteolytic enzymes have been described in many publications since the initial article by Lo, et al., including U.S. Pat. No. 3,910,296 (Karageozian, et al.).

Numerous compositions and methods for disinfecting contact lenses have also been described. Those methods may be generally characterized as involving the use of heat and/or chemical agents. Representative chemical agents for this purpose include organic antimicrobials such as benzalkonium chloride and chlorhexidine, and inorganic antimicrobials such as hydrogen peroxide and peroxide-generating compounds. U.S. Pat. Nos. 4,407,791 and 4,525,346 (Stark) describe the use of polymeric quaternary ammonium compounds to disinfect contact lenses and to preserve contact lens care products. U.S. Pat. Nos. 4,758,595 and 4,836,986 (Ogunbiyi) describe the use of polymeric biguanides for the same purpose.

Various methods for cleaning and disinfecting contact lenses at the same time have been proposed. Methods involving the combined use of proteolytic enzymes and peroxides to clean and disinfect contact lenses simultaneously, are described in U.S. Pat. No. Re 32,672 (Huth, et al.). A representative method of simultaneously cleaning and disinfecting contact lenses involving the use of proteolytic enzymes and quaternary ammonium compounds is described in Japanese Patent Publication 57-24526 (Boghosian, et al.). The combined use of a biguanide (i.e., chlorhexidine) and liquid enzyme compositions to simultaneously clean and disinfect contact lenses is described in Canadian Patent No. 1,150,907 (Ludwig, et al.). Methods involving the combined use of dissolved proteolytic enzymes to clean and heat to disinfect are described in U.S. Pat. No. 4,614,549 (Ogunbiyi). The combined use of proteolytic enzymes and polymeric biguanides or polymeric quaternary ammonium compounds is described in copending, commonly assigned U.S. patent application Ser. No. 08/156,043 and in corresponding European Patent Application Publication No. 0 456 467 A2 (Rosenthal, et al.), as well as in U.S. Pat. No. 5,096,607 (Mowrey-McKee, et al.).

The commercial viability of most prior enzyme cleaning products has depended on the use of stable enzyme tablets. More specifically, the use of solid enzymatic cleaning compositions has been necessary to ensure stability of the enzymes prior to use. In order to use such compositions, a separate packet containing a tablet must be opened, the tablet must be placed in a separate vial containing a solution, and the tablet must be dissolved in order to release the enzyme into the solution. This practice is usually performed only once a week due to the cumbersome and tedious procedure and potential for irritation and toxicity. Moreover, the enzymatic cleaning tablets contain a large amount of excipients, such as effervescent agents (e.g., bicarbonate) and bulking agents (e.g., sodium chloride).

There have been prior attempts to use liquid enzyme compositions to clean contact lenses. However, those attempts have been hampered by the fact that aqueous liquid enzyme compositions are inherently unstable. When a proteolytic enzyme is placed in an aqueous solution for an extended period (i.e., several months or more), the enzyme may lose all or a substantial portion of its proteolytic activity. Steps can be taken to stabilize the compositions, but the use of stabilizing agents may have an adverse effect on the activity of the enzyme. For example, stabilizing agents can protect enzymes from chemical instability problems during storage in an aqueous liquid, by placing the enzymes in a dormant physical conformation. However, such agents may also inhibit the ability of the enzymes to become active again at the time of use. Finally, in addition to the general problems referred to above, a commercially viable liquid enzyme preparation for treating contact lenses must be relatively nontoxic, and must be compatible with other chemical agents used in treating contact lenses, particularly antimicrobial agents utilized to disinfect the lenses.

The following patents may be referred to for further background concerning prior attempts to stabilize liquid enzyme formulations: U.S. Pat. No. 5,281,277 (Nakagawa) and U.S. Pat. No. 5,314,823 (Nakagawa) and Japanese Kokai Patent Applications Nos. 92-370197; 92-143718; 92-243215; and 89-180515 describe liquid enzyme compositions for treating contact lenses. The compositions of the present invention are believed to provide significant improvements relative to the compositions described in those publications.

Recently, U.S. Pat. Nos. 5,576,278, 5,604,190, 5,605,661, 5,672,213 5,718,895 and 5,723,421 were issued to Alcon Laboratories, Inc. These patents disclose advanced liquid enzyme compositions particularly suited for contact lens care. The present invention improves on such compositions by providing compositions containing alkyl trypsin enzymes. The alkyl trypsins were discovered to possess superior stability in contact lens care compositions, over native or modified enzymes used in the art.

SUMMARY OF THE INVENTION

The present invention is directed to alkyl trypsin compositions and methods of use in cleaning and disinfecting contact lenses. Alkyl trypsins were discovered by the inventors to possess superior proteolytic stability in a solubilized state suitable for contact lens care use. The inventors have also found that, unlike other highly stable proteases, alkyl trypsins are physiologically well tolerated.

The compositions of the present invention are either formulated as alkyl trypsin concentrates or as alkyl trypsin multi-purpose solutions. The concentrates are employed as single dose cleaning compositions in conjunction with an aqueous solvent, e.g., a disinfecting solution. Prior to each cleaning or cleaning and disinfecting session, the user adds a small amount of the alkyl trypsin concentrate to the aqueous diluting solution. The soiled contact lenses may then be soaked in the resultant diluted enzyme solution for a time sufficient to clean or clean and disinfect the lens. Due to the inherent instability of solubilized enzymes, however, prior liquid enzyme concentrates have only been able to provide a limited storage shelf-life. Thus, one object of the present invention is to provide liquid enzyme concentrates with extended shelf-lives.

Multi-purpose solutions provide a complete solution containing a disinfectant and a cleaning enzyme for the simultaneous cleaning and disinfecting of contact lenses. Multi-purpose solutions are prepared by the addition of a large bolus of protease to a requisite amount of disinfecting diluent. The mixed, ready-to-use multi-purpose solution may now be used over a period of time for the periodic cleaning and disinfecting of contact lenses. Due to the inherent instability of an enzyme in an aqueous environment, however, prior multi-purpose solutions have not yet provided a useful product life for the consumer. Thus, another object of the present invention is to provide multi-purpose compositions with prolonged shelf-lives, both for the pre-mixed components, as well as the mixed, ready-to-use compositions.

The inventors have thus found that alkyl trypsin containing liquid enzyme compositions possess significantly enhanced shelf-lives. With this discovery, liquid enzyme compositions possessing longer shelf-lives can now be provided to the consumer.

The liquid alkyl trypsin compositions of the present invention may also exhibit superior safety profiles over prior liquid enzyme compositions containing conventional enzymes.

The alkyl trypsin compositions of the present invention are formulated as either concentrated liquids or solids (either as a multiple dosing composition or as a pre-mixed cleaning component of a multi-purpose solution). While various other components may be included in the concentrated liquid alkyl trypsin compositions of the present invention, preferred compositions will also contain a 2–3 carbon polyol, a borate/boric acid compound and calcium ion. The addition of those components provides for even greater stabilization of the alkyl trypsin.

The present invention also provides methods for cleaning contact lenses with the above-described alkyl trypsin compositions. Generally, in order to clean a soiled lens, the lens is placed in a few milliliters of an aqueous solution and a small amount, generally one to two drops or a tablet of a concentrated alkyl trypsin composition is added to the solution. The lens is then soaked in the resultant cleaning solution for a time sufficient to clean the lens. Alternatively, as stated above, contact lenses may be cleaned by immersion in a multi-purpose solution containing an alkyl trypsin.

The compositions and methods of the present invention provide greater ease of use. This ease of use enables contact lens users to clean their lenses 2 to 3 times a week, or more preferably, every day. It has been found that daily use of the compositions of the present invention results in dramatically better cleaning and safety, as compared to the once-a-week enzyme cleaning regimens.

DETAILED DESCRIPTION OF THE INVENTION

Figure 1:
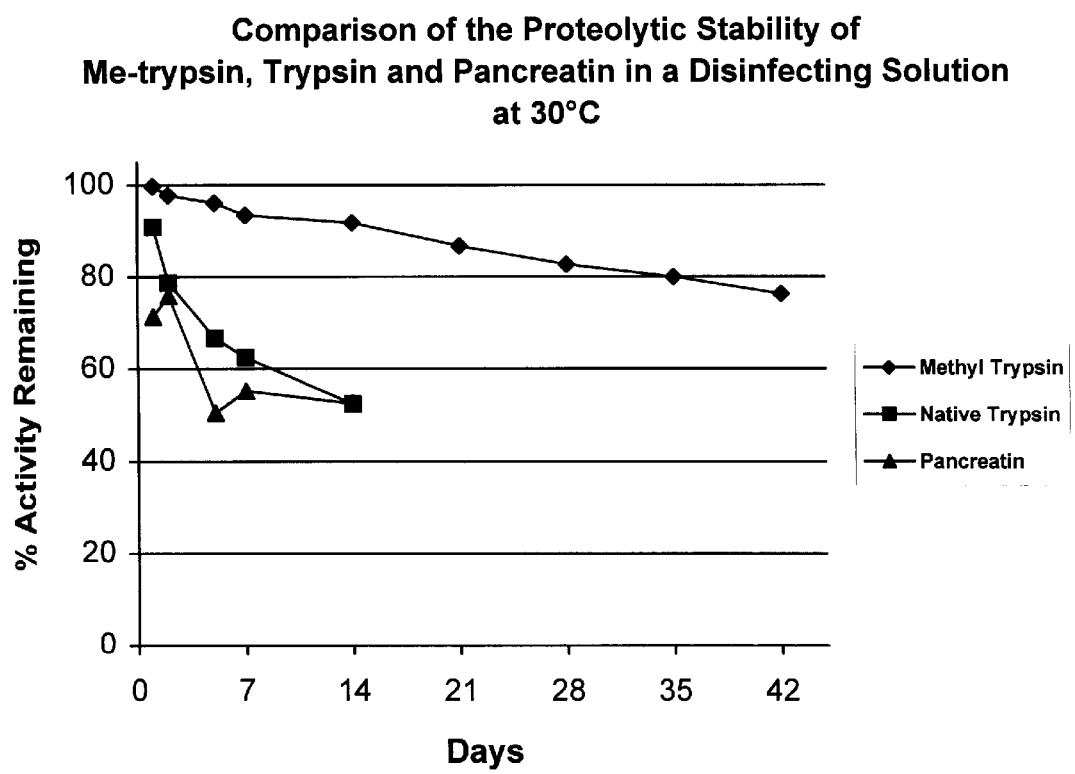
FIG. 1 is a graph comparing the proteolytic stability of methyl trypsin, trypsin and pancreatin in a disinfecting solution stored at 30° C. through 42 days.

It has been discovered that alkyl trypsins are more stable in liquid compositions than the native trypsin, or other native enzymes. As stated above, this is particularly important in the formulation of liquid enzyme concentrates and multi-purpose solution useful in cleaning or cleaning and disinfecting contact lenses.

As used herein, "Al-trypsin" refers to a covalently modified trypsin wherein one or more of its lysine epsilon-amino groups has been mono-alkylated or di-alkylated to form the corresponding monoalkylamino or dialkylamino group. The alkyl group attached to the amine may be a primary or branched $C_{1-12}$ group. Preferred Al-trypsins of the present invention are those wherein the alkyl group is a primary or branched $C_{1-4}$ group. Alkylation of trypsin is generally performed by reductive alkylation. The degree of alkylation of the lysine epsilon-amino groups will depend on the reaction conditions of the reductive alkylation process. For example, if the reaction cycle is repeated a number of times and/or a higher reagent to enzyme ratio is used, then full alkylation, i.e., alkylation of all of the lysine epsilon-amino groups, will tend to be achieved. Al-trypsins of the present invention will preferably be fully dialkylyated at all of their lysine epsilon-amino groups. The most preferred Al-trypsin is methyl trypsin ("Me-trypsin"). The most preferred Me-trypsin of the present invention will be derived from porcine tissue sources and will be fully dimethylated, as described above.

Trypsin is a 23,800 dalton protease with 6 disulfide bridges. Trypsin can be synthesized or obtained from various sources, such as porcine, bovine or swine pancreatin. Trypsin is also available from commercial sources such as Sigma Chemical Co. (St. Louis, Mo.), Biofac Co. (United Kingdom) and Novo Nordisk (Denmark). Trypsin may vary from species to species, but in general will be highly homologous with porcine or human trypsin.

Al-trypsin can be synthesized by the process of reductive alkylation of trypsin, as generally described in Scheme 1, below.

Scheme 1:

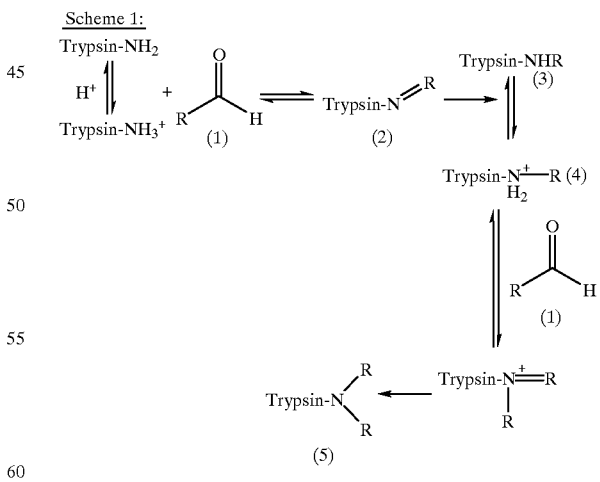

wherein, R is branched or unbranched $C_{1-12}$ alkyl.

As illustrated in scheme 1, the epsilon amino group of the lysine residues of trypsin is reacted with aldehydic alkylating reagent (1) to afford the alkylimino product (2). The alkylimino product (2) reduces to the resonant alkylamino species (3,4). The product (3,4) may react with another mole of the alkylating reagent (1) to yield the dialkylamino trypsin (5). As illustrated above, the resultant alkylated trypsin may either be mono or dialkylated at the lysine epsilon-amino groups.

EXAMPLE 1

Me-trypsin may be prepared by the following synthesis: The following solutions are first prepared:
1. Borate buffer: 0.2 M sodium borate buffer, pH 9.2 containing 2 mg/ml benzamidine hydrochloride and a trace amount of n-octanol.
2. Trypsin: 1 g in 150 ml borate buffer.

To the 150 ml solution of trypsin, 10 ml of 1 M sodium borohydride is added followed quickly by 10 ml of 2.4 M formaldehyde. Three more volumes of sodium borohydride and formaldehyde are added at 10 minute intervals. The reaction solution is then acidified with glacial acetic acid to approximately pH 4.2 and then dialyzed extensively against 2 mM HCl at 4° C. (8 changes of 2 L each within 24 hours). The dialyzed solution is finally lyophilized for over 20 hours.

The above reactions are further described in Rice, R H, Means, G E and Brown, W D. Stabilization of bovine trypsin by reductive methylation, *Biochimica et Biophysica Acta*, volume 492, pages 316–321 (1977); and Means, G E and Feeney, R E. Reductive alkylation of amino groups in proteins, *Biochemistry*, volume 7, pages 2192–2210 (1968). Me-trypsin is also available from commercial sources such as Sigma Chemical Co. and Promega Corp. (Madison, Wis.).

Other Al-trypsins may be prepared by methods analogous to Example 1, wherein formaldehyde is replaced by other alkylating reagents. For example, ethyl trypsin ("Et-trypsin") may be synthesized by an analogous method described in Example 1 and Scheme 1 above, wherein acetaldehyde is used as the alkylating reagent in place of formaldehyde.

Al-trypsin compositions of the present invention are initially stabilized in concentrated form. The Al-trypsin concentrate may be formulated as a powder, tablet or liquid. Dry powder or tablet compositions may be preferred when the Al-trypsin concentrates need to be stable for longer periods of time than liquids. Excipients which make up the enzyme powder compositions are known in the art. Generally, the Al-trypsin composition will include bulking agents to carry the relatively small volume of Al-trypsin into the diluting solution. Such bulking agents typically include polyols (e.g., mannitol or soribitol), polyethylene glycols (molecular weights greater than 1000) and sugars. Other excipients may include salts such as NaCl, chelating agents such as EDTA, and buffering agents such as Tris. Other additives may include surfactants to ease dispersion and dissolution of the powder in water. Preferred Al-trypsin compositions comprise mannitol and polyethylene glycol-5000 (PEG-5000).

Enzyme tablet compositions and methods of manufacturing are known in the art. Enzyme tablets require the use of bulking agents and binding agents. Additionally, tablets may contain effervescing agents such as bicarbonate to expedite dissolution of the tablet into the diluting solution. Other excipients known in the art may be added to provide greater consistency and easier manufacture of the tablets. Preferred Al-trypsin tablet compositions comprise sodium bicarbonate, citric acid, PEG-8000, carboxymethyl cellulose and lactose.

Liquid Al-trypsin compositions are preferred concentrated compositions of the present invention due to their ease of preparation, sterilization, dispensing within the enzyme container of a bottle assembly, as well as user convenience.

Liquid Al-trypsin compositions are solubilized in a suitable liquid vehicle. As used herein, "suitable liquid vehicle" refers to an aqueous or non-aqueous composition which, when diluted with an aqueous solvent described below, is compatible with the requirements of contact lens care regimens.

Concentrated non-aqueous enzyme compositions of the present invention generally comprise a crystalline enzyme uniformly dispersed in a water-soluble organic liquid. Typical organic liquids include polyoxyethylene glycols (e.g., PEG-400) and alkoxy polyoxyethylene glycols such as methoxy polyethylene glycols. In this composition, the enzyme is in a dormant state, suspended within the non-aqueous liquid. Following dissolution in an aqueous diluting composition, the enzyme solubilizes and becomes active. Preferred non-aqueous enzyme compositions comprise an Al-trypsin dispersed in PEG-400.

It has been found that the use of a concentrated aqueous vehicle containing a water-miscible organic molecule further enhances the stability of an Al-trypsin. The use of this type of vehicle is therefore preferred. As used herein, the term "water-miscible organic molecule" or "stabilizer," refers to an organic compound that forms one liquid phase with water when added to water. While not intending to be bound by any theory, it is believed that the stabilizers compete with water in the hydrogen bonding of the enzyme in solution, and thereby deprive the enzyme of the water-hydrogen bonding necessary for enzyme activity. Therefore, the particular structure of the stabilizer is generally not an important factor to stabilization efficacy. It is rather the ability of the organic molecule to form one phase with water that determines its stabilizing utility in the present invention. Furthermore, the stabilizers must also be suitable for ophthalmic use and will thus exhibit minimal adverse effects in the cleaning or cleaning and disinfecting regimen. For example, the stabilizer will not contribute to ocular irritation/toxicity or interfere with the anti-microbial efficacy of an anti-microbial agent. Given the above criteria, various and numerous molecules may be used in the present invention to stabilize an Al-trypsin.

The stabilizers will be employed in the aqueous concentrates of the present invention in an amount of from 10–90% weight/volume ("w/v"), and preferably, in an amount of from 40–80% (w/v). In general, the stabilizers will be polar, non-volatile, non-ionic or amphoteric molecules. Examples of stabilizers include polyols (polymers and monomers), and poorly metabolized sugars, including disaccharide or monomeric sugars. The above stabilizers are well known in the art and are available from numerous commercial sources. Examples of polymeric polyols are polyethylene glycol 200 (PEG 200) and PEG 400.

The preferred polyols utilized in the concentrated compositions of the present invention are 2–3 carbon polyols. As used herein, the term "2–3 carbon polyol" refers to a compound with 2 to 3 carbon atoms and at least two hydroxy groups. Examples of 2–3 carbon polyols are glycerol, 1,2-propane diol ("propylene glycol"), 1,3-propane diol and ethylene glycol. Propylene glycol is the preferred 2–3 carbon polyol.

Preferred concentrated compositions of the present invention will also include an effective amount of a borate/boric acid compound. As used herein, "borate/boric acid compound" refers to an inorganic compound comprising boron and one or more oxygen groups, and which is either in acid or base form when dissolved in a composition of the present invention. Sources of borate/boric acid compounds include alkali metal salts of borate, boric acid and borax. As used herein, "effective amount of a borate/boric acid compound" refers to that amount of a borate/boric acid compound contained in a concentrated Al-trypsin composition which enhances the proteolytic stability of an Al-trypsin. While such an amount will vary depending on other components present in the concentrate, the amount will be about 0.3 to 8.0% (w/v). Preferred amounts will be of from 0.5 to 1.5% (w/v). The borate/boric acid compound may also contribute to the anti-microbial preservation of the liquid enzyme compositions of the present invention to a level effective for multi-use dispensing. The solubility of the borates may be limited in water. The solubility of these compounds, however, may be increased by increasing the amount of polyol employed.

The preferred concentrated compositions of the present invention will also contain an effective amount of calcium ion. The calcium ion contained in the compositions of the present invention may be obtained by the addition of various calcium salts. For example, the calcium ion source may be obtained from calcium chloride, calcium acetate and calcium ascorbate or other water soluble salts of calcium. The most preferred calcium ion source is calcium chloride. As used herein, "effective amount of calcium ion" refers to that amount of calcium ion which enhances the proteolytic stability of Al-trypsin in the concentrated compositions of the present invention. While that amount will vary depending upon the various components present, typical calcium ion concentrations will be about 1 to 90 millimolar. Preferred concentrations will be about 4.5 to 45 millimolar, and most preferred concentrations will be of from 10 to 25 millimolar.

The concentrated compositions of the present invention may also include an acidic compound. Examples of acidic compounds include alkyl ($C_1$ to $C_6$) carboxylic acid compounds, such as formic, acetic and propionic acids, as well as other acids, such as aromatic carboxylic and aromatic sulfonic acids. The solubility of the acids may be limited in water. However, the solubility of these compounds may be increased by increasing the amount of polyol employed.

Other agents may also be employed in the concentrates of the present invention. For example, other divalent cations, such as magnesium, may also be employed. The compositions may additionally contain preservatives for compositions intended for multi-dosing. Examples of suitable preservatives include sorbic acid and salts of sorbic acid, chlorhexidine, parabens as well as those antimicrobial agents detailed below as being useful as disinfectants in the cleaning and disinfecting methods of the present invention. Still other agents may be added to the present invention including pH adjusting agents such as triethanolamine, Tris, HCl, or NaOH, and surfactants such as cationic, non-ionic, or amphoteric compounds.

Preferred present invention concentrates containing a monomeric polyol will contain an effective amount of an Al-trypsin, about 40–60% (w/v) of a 2–3 carbon polyol, 0.5–1.5% (w/v) of a borate/boric acid compound, 0.1–0.25% (w/v) calcium chloride and water. The most preferred composition of this type will contain an effective amount of an Al-trypsin, 50% (w/v) propylene glycol, 1.5% (w/v) sodium borate, 0.25% (w/v) calcium chloride and water.

Preferred present invention concentrates containing both a monomeric and polymeric polyol will contain an effective amount of an Al-trypsin, about 15–25% (w/v) of a 2–3 carbon polyol, 25–50% (w/v) of a polymeric polyol, 0.5–1.5% (w/v) of a borate/boric acid compound, 0.1–0.25% (w/v) calcium chloride and water. The most preferred composition of this type will contain an effective amount of an Al-trypsin, 25% (w/v) glycerol, 50% (w/v) PEG-400, 1.5% (w/v) sodium borate, 0.25% (w/v) calcium chloride and water.

The concentrated Al-trypsin compositions of the present invention will have an Al-trypsin concentration sufficient to provide an effective amount of enzyme to clean a lens when a small amount of the composition is added to a diluent. Alternatively, the multi-purpose compositions of the present invention will have an enzyme concentration sufficient to provide an effective amount of enzyme to clean the lens without further dilution. As used herein, such an amount is referred to as "an amount effective to clean the lens." The amount of enzyme used in the concentrated liquid enzyme compositions and multi-purpose compositions will generally range from about 0.05 to 2% w/v and about 0.0005 to 0.2% w/v, respectively. The selection of a specific concentration will depend on various factors, such as: the specific Al-trypsin or combination of AL-trypsins employed and the purity of the Al-trypsins; the type of lenses to be cleaned (e.g., "hard" vs. "soft contact lenses); the intended frequency of cleaning (e.g., daily or weekly); potential interference of the Al-trypsin with an antimicrobial agent; ocular irritation/toxicity potential of the Al-trypsin; the intended duration of each cleaning; and, with concentrated compositions, the amount of enzyme composition and amount of diluent used.

During storage, some of the activity of the enzyme may be lost, depending on length of storage and temperature conditions. Thus, the concentrated Al-trypsin compositions of the present invention may be prepared with initial amounts of enzyme that exceed the concentration ranges described herein. The preferred liquid concentrated compositions of the present invention will generally contain an Al-trypsin in an amount of about 300–6000 PAU/mL. The concentrated compositions will most preferably contain about 900–2200 PAU/mL, which corresponds to an Al-trypsin in the range of about 0.1 to 1.0% w/v for liquid concentrates. Following dilution of the enzyme concentrate in an aqueous diluent or, in the case of a multi-purpose solution, the concentration of the Al-trypsin will range from about 1–100 PAU/mL, and preferably from about 5–25 PAU/mL. For purposes of this specification, a "proteolytic activity unit" or "PAU" is defined as the amount of enzyme activity necessary to generate one microgram (mcg) of tyrosine per minute ("mcg Tyr/min"), as determined by the casein-digestion, colorimetric assay described below.

Casein-digestion Assay

A 5.0 mL portion of casein substrate (0.65% casein w/v) is equilibrated for 10 minutes ("min")±5 seconds ("sec") at 37° C. A 1.0 mL portion of enzyme solution (0.2 mg/ml) is then added to the casein substrate and the mixture vortexed, then incubated for 10 min±5 sec at 37° C. After incubation, 5.0 mL of 14% trichloroacetic acid is added and the resultant mixture immediately vortexed. The mixture is incubated for at least another 30 min, then vortexed and centrifuged for 15–20 min (approx. 2000 rpm). The supernatant of the centrifuged sample is filtered into a serum filter sampler and a 2.0 mL aliquot removed. To the 2.0 mL sample is added 5.0 mL of 5.3% $Na_2CO_3$. The sample is vortexed, 1.0 mL of 0.67 N Folin's Phenol reagent is added, and the sample is immediately vortexed again, then incubated for 60 min at 37° C. The sample is then read on a visible light spectrophotometer at 660 nanometers versus purified water as the reference. The sample concentration is then determined by comparison to a tyrosine standard curve.

As stated above, the Al-trypsin concentrates may be included in a multi-purpose solution. The multi-purpose solutions of the present invention comprise a two-part system. The first part ("Part I") is a sterile, concentrated Al-trypsin composition and the second part ("Part II") is a sterile diluting composition. An antimicrobial agent is further required, and may be included in either composition.

The multi-purpose solutions of the present invention require the use of a two-compartment device to store and mix the sterile two-part system, and to dispense the resultant sterile multi-purpose composition. Various devices may be employed, but the central features of the device are that it provides separate component storage, a means for aseptically adding one component to the other component, a mixing chamber and a dispensing means, all in a single bottle assembly. PCT Publication No. WO 98/25650, incorporated herein by reference, discloses preferred two-part devices useful in preparing multi-purpose solutions of the present invention.

The resultant multi-purpose composition may contain various other agents, but will contain: 1) an anti-microbial agent, 2) an Al-trypsin, 3) a buffering agent, 4) a tonicity agent, and 5) water. The multi-purpose compositions of the present invention are intended to function as storing, rinsing, cleaning and disinfecting solutions. Therefore, the multi-purpose compositions will be physiologically compatible with the eye.

The Part I Al-trypsin compositions of the present invention comprise an Al-trypsin, stabilizers and other excipients. Any of the above-described Al-trypsin concentrates may be employed as a Part I composition. The Part II compositions may be any of the aqueous diluents or disinfecting solutions discussed below. As stated above, the disinfecting (antimicrobial) agents may be contained in either the Part I or Part II component of the multi-purpose solution.

The cleaning methods of the present invention utilize an aqueous solvent. The aqueous solvent may contain various salts such as sodium chloride and potassium chloride, buffering agents such as boric acid and sodium borate, and other agents such as chelating agents and preservatives. An example of a suitable aqueous solvent is a saline solution, such as Unisol® Plus Solution (registered trademark of Alcon Laboratories, Inc.).

The cleaning and disinfecting methods of the present invention employ a disinfecting solution as the aqueous diluent for the dilution of the Al-trypsin concentrate. The disinfecting solution will contain at least one anti-microbial agent, as discussed below.

Antimicrobial agents may be oxidative, such as hydrogen peroxide, or non-oxidative polymeric antimicrobial agents which derive their antimicrobial activity through a chemical or physicochemical interaction with the organisms. As used in the present specification, the term "polymeric antimicrobial agent" refers to any nitrogen-containing polymer or co-polymer which has antimicrobial activity. Preferred polymeric antimicrobial agents include: polyquaternium-1, which is a polymeric quaternary ammonium compound; and polyhexamethylene biguanide ("PHMB") or polyaminopropyl biguanide ("PAPB"), which is a polymeric biguanide. These preferred antimicrobial agents are disclosed in U.S. Pat. Nos. 4,407,791 and 4,525,346, issued to Stark, and U.S. Pat. No. 4,758,595 and 4,836,986, issued to Ogunbiyi, respectively. The entire contents of the foregoing publications are hereby incorporated in the present specification by reference. Other antimicrobial agents suitable in the methods of the present invention include: other quaternary ammonium compounds, such as benzalkonium halides, and other biguanides, such as chlorhexidine. The antimicrobial agents used herein are preferably employed in the absence of mercury-containing compounds such as thimerosal.

The most preferred antimicrobial agents are polymeric quaternary ammonium compounds of the structure:

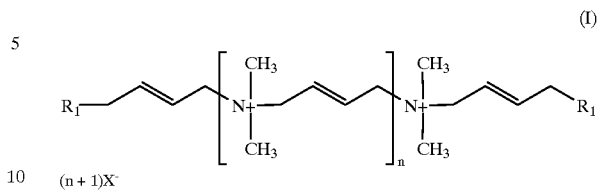

(I)

(n + 1)X⁻ wherein:
$R_1$ and $R_2$ can be the same or different and are selected from:
$N^+(CH_2CH_2OH)_3X^-$,
$N(CH_3)_2$ or OH;
$X^-$ is a pharmaceutically acceptable anion, preferably chloride; and
n=integer from 1 to 50.

The most preferred compounds of this structure is polyquaternium-1, which is also known as Onamer M™ (registered trademark of Onyx Chemical Corporation) or as Polyquad® (registered trademark of Alcon Laboratories, Inc.). Polyquaternium-1 is a mixture of the above referenced compounds, wherein $X^-$ is chloride and $R_1$, $R_2$ and n are as defined above.

The above-described antimicrobial agents are utilized in the methods of the present invention in an amount effective to eliminate substantially or to reduce significantly the number of viable microorganisms found on contact lenses, in accordance with the requirements of governmental regulatory agencies, such as the United States Food and Drug Administration. For purposes of the present specification, that amount is referred to as being "an amount effective to disinfect" or "an antimicrobially effective amount." The amount of antimicrobial agents employed will vary, depending on factors such as the type of lens care regimen in which the method is being utilized. For example, the use of an efficacious daily cleaner in the lens care regimen may substantially reduce the amount of material deposited on the lenses, including microorganisms, and thereby lessen the amount of antimicrobial agents required to disinfect the lenses. The type of lens being treated (e.g., "hard" versus "soft" lenses) may also be a factor. In general, a concentration in the range of about 0.000001% to about 0.01% w/v of one or more of the above-described antimicrobial agents will be employed. The most preferred concentration of the polymeric quaternary ammonium compounds of Formula (I) in the disinfecting or multi-purpose compositions is about 0.001% w/v.

Oxidative disinfecting agents may also be employed with the Al-trypsin concentrates, for simultaneous cleaning and disinfecting. Such oxidative disinfecting agents include various peroxides which yield active oxygen in solution. Preferred methods will employ hydrogen peroxide in the range of 0.3 to 3.0% w/v to disinfect the lens. Methods utilizing an oxidative disinfecting system are described in U.S. Pat. No. Re 32,672 (Huth, et al.), the entire contents of which are hereby incorporated in the present specification by reference.

As will be appreciated by those skilled in the art, the disinfecting solutions utilized in the present invention may contain various components in addition to the above-described antimicrobial agents. In general, the disinfecting solution may also contain sodium chloride and other excipients which together provide an ophthalmically compatible solution. As will be appreciated by those skilled in the art, the disinfecting solutions utilized in the present invention may contain various other components such as suitable buffering agents, chelating and/or sequestering agents and tonicity adjusting agents. The disinfecting compositions may also contain surfactants. In general, the disinfecting compositions will contain one or more anti-microbial agents (e.g., PHMB or polyquaternium-1), a buffer (e.g., borate), citrates, tonicity agents (e.g., NaCl, sugars), a chelating agent (e.g., EDTA), and surfactants (e.g., block copolymers). Other agents which enhance the anti-microbial efficacy of the compositions, such as amino alcohols and alkylamines, may also be added. Preferred disinfecting compositions comprise polyquaternium-1, sodium borate, boric acid, propylene glycol and Pluronic P-103. The most preferred disinfecting compositions comprise boric acid, sorbitol, 95% 2-amino-2-methyl-1-propanol ("AMP-95"), sodium citrate, sodium chloride, disodium edetate, polyquaternium-1, poloxamer 1304 ("Tetronic 1304") and myristamidopropyl diamethyl amine ("MAPDA").

The ionic strengths preferably utilized in the cleaning and disinfecting methods of the present invention generally correspond to tonicities/osmolalities in the range of hypotonic to isotonic, and more preferably in the range of 150 to 350 milliOsmoles per kilogram (mOs/kg). A range of 200 to 300 mOs/kg is particularly preferred, and an osmolality of about 220 mOs/kg is most preferred.

The methods of the present invention will typically involve adding a small amount of an Al-trypsin concentrate to about 2 to 10 mL of an aqueous solvent or disinfecting solution, placing the soiled lens into the enzyme/solvent or enzyme/disinfectant solution, and soaking the lens for a period of time effective to clean or clean and disinfect the lens. The amount of liquid Al-trypsin concentrate utilized will vary based on factors such as the amount of aqueous solvent or disinfecting solution used, but generally will be about 1 to 2 drops. Preferred methods involve adding I drop (approximately 30–40 μL) to 5 mL of aqueous solvent or disinfecting solution. Similarly, the amount of a solid Al-trypsin concentrate added to the aqueous disinfecting solution will vary. Preferred methods involve adding about 50 milligrams (generally 1 tablet) to 5 mL of aqueous solvent of disinfecting solution. The soiled lens can be placed in the aqueous solvent or disinfecting solution either before or after the addition of the liquid enzyme composition. Optionally, the contact lenses are first rubbed with a non-enzymatic daily surfactant cleaner prior to immersion in the enzyme/solvent or enzyme/disinfectant solution. The lens will typically be soaked overnight, but shorter or longer durations are contemplated by the methods of the present invention. A soaking time of 4 to 8 hours is preferred. The methods of the present invention allow the above-described regimen to be performed once per week, but more preferably, every day.

Alternatively, the lenses may be cleaned and disinfected by soaking the lens in about 2 to 10 mL of a multi-purpose solution for about 4–8 hours, or overnight.

The following examples are presented to illustrate further, various aspects of the present invention, but are not intended to limit the scope of the invention in any respect. As used below, the terms "Part I Al-trypsin composition" or "Part I composition" refer to either a stand-alone, multi-dosing, concentrated Al-trypsin composition or a "Part I" component of a multi-purpose composition of the present invention, as those terms are described above. As used below, the terms "Part II disinfecting composition" or "Part II composition" refer to either a stand-alone disinfecting solution or a "Part II" component of a multi-purpose composition of the present invention, as those terms are described above.

EXAMPLE 2

A preferred Part I Al-trypsin composition and a preferred Part II disinfecting composition are described below:

A. Part I Me-Trypsin Composition

| Ingredient | Amount |
| --- | --- |
| Me-Trypsin | 3000 PAU/mL |
| Boric acid | 1.5% (w/v) |
| Propylene glycol | 50% (w/v) |
| Calcium chloride | 0.25% (w/v) |
| NaOH/HCl | QS to adjust pH to 6 to 8 |
| Purified water | QS |

To prepare the Me-trypsin concentrate, calcium chloride and boric acid are first dispersed in about 30% of the volume of purified water. Propylene glycol is then added. The pH of the solution is adjusted, and Me-trypsin is then dissolved in the solution, followed by a final volume adjustment with purified water. The composition is then sterile filtered using a 0.2 μm filter.

B. Part II Disinfecting Composition

| Ingredient | Amount % (w/v) |
| --- | --- |
| Polyquaternium-1 | 0.001 |
| Boric acid | 0.6 |
| Sodium chloride | 0.1 |
| AMP-95 | 0.45 |
| MAPDA | 0.0005 |
| Sorbitol | 1.2 |
| Sodium citrate | 0.65 |
| Tetronic 1304 | 0.05 |
| Disodium Edetate | 0.05 |
| NaOH/HCl | To adjust pH 6.5 to 8.0 |
| Purified water | QS |

To prepare the disinfecting composition, the ingredients are dissolved with 90% of the volume of purified water, the pH is adjusted, and the volume is then brought up to 100% volume. The composition is then sterile filtered using a 0.2 μm membrane filter.

Various volumes of the above Part I and Part II compositions may be employed in a single used cleaning and disinfecting composition. Preferred amounts include adding 1 drop of the Part I composition to about 5 mL of the Part II composition. Alternatively, various volumes of the above Part I and Part II compositions may be employed in a two-compartment bottle assembly of the present invention. Preferred amounts include 1 mL of the enzyme composition and 120 mL of the disinfecting composition.

EXAMPLE 3

The following are examples of Part I Al-trypsin compositions of the present invention:

A. Part I Me-trypsin Composition

| Ingredient | Amount |
| --- | --- |
| Me-trypsin | 2200 PAU/mL |
| Sodium borate | 1.5% (w/v) |
| Glycerol | 25% (w/v) |
| PEG-400 | 50% (w/v) |
| POLYQUAD ® | 0.003% (w/v) |
| NaOH/HCl | QS to pH 5 to 8 |
| Calcium chloride | 0.25% (w/v) |
| Water | QS |

The above formulation is prepared by first sequentially mixing glycerol, PEG-400, POLYQUAD®, purified water, hydrochloric acid and sodium borate together. The required amount of trypsin (about 0.3 w/v) is then dissolved the above mixture, the pH is adjusted and the solution is brought to 100% volume. The enzyme composition is then sterile filtered (0.2 μm filter). The optimal pH of the above formulation will be in the range of 6–7; a pH of 6.5 is most preferred.

B. Part I Me-trypsin Composition

| Ingredient | Amount |
| --- | --- |
| Me-Trypsin | 2200 PAU/mL |
| Sodium borate | 7.62% (w/v) |
| Propylene glycol | 50% (v/v) |
| Water | QS |
| NaOH/HCl | QS to pH 6.0 |

The above composition may be prepared by methods analogous to those described in Example 3A.

C. Part I Et-trypsin Composition

| Ingredient | Amount |
| --- | --- |
| Et-Trypsin | 3000 PAU/mL |
| Boric acid | 1.5% (w/v) |
| Propylene glycol | 50% (w/v) |
| Calcium chloride | 0.25% (w/v) |
| NaOH/HCl | QS to adjust pH to 6 to 8 |
| Purified water | QS |

The above composition may be prepared by methods analogous to those described in Example 3A.

EXAMPLE 4

The following are examples are preferred Part I solid Me-trypsin compositions intended for use in the preparation of multi-purpose compositions of the present invention.

A. Part I Me-Trypsin Tablet Composition

| Ingredient | Amount |
| --- | --- |
| Me-Trypsin | 4000 PAU |
| Sodium bicarbonate | 8.5 mg |
| Citric acid | 3.5 mg |
| PEG-3350 | 3.0 mg |
| Lactose | QS to 50 mg |

The tablets are generally prepared by first mixing the appropriate amounts of each of the ingredients and then passing the mixture through an oscillating granulator equipped with a 20 mesh hard screen. The screened ingredients are then added to a suitably sized blender and mixed for 30 minutes. An appropriate amount of PEG and Me-trypsin are then passed through a 20 mesh hard screen and this mixture is then added to the blender. The combined screened ingredients are then blended for an additional 15 minutes. Using a tablet press equipped with a 5/32" tooling, the blended ingredients are then compressed into tablets having a target weight of 50–80 mg and a hardness of 8 SCU. The tablets may then be sterilized by the method of gamma-sterilization.

B. Part I Me-Trypsin Powder Composition

| Ingredient | Amount |
| --- | --- |
| Me-trypsin | 3000 PAU (~3–4 mg) |
| Lactose | QS to 1 g |

The enzyme and lactose are dissolved in water (1 g of enzyme/lactose per 1 mL of water) and sterile filtered using a 0.2 μm filter. The sterile enzyme solution as then aseptically lyophilized.

The above Me-trypsin concentrated solid compositions may be preferably combined with about 120 mL of a Part II disinfecting solution to form a multi-purpose composition.

EXAMPLE 5

The following are examples of Part II disinfecting compositions useful in the methods of the present invention:

A. Part II Disinfecting Composition

| Ingredient | Amount (w/v) |
| --- | --- |
| Polyquaternium-1 | 0.0002% |
| Sodium borate | 0.25% |
| Propylene glycol | 1.0% |
| Pluronic P-103 | 0.1% |
| NaOH/HCl | To adjust pH to 6.5 to 8.0 |
| Purified water | QS |

B. Part II Disinfecting Composition

| Ingredient | Amount (w/v) |
| --- | --- |
| PHMB | 0.0001% |
| Sodium phosphate | 0.28% |
| Potassium phosphate | 0.06% |
| Sodium chloride | 0.7% |
| Disodium edetate | 0.05% |
| NaOH/HCl | To adjust to pH 6.5 to 8.0 |
| Purified water | QS |

C. Part II Disinfecting Composition

| Ingredient | Amount % (w/v) |
| --- | --- |
| Polyquaternium-1 | 0.001 + 10% excess |
| Sodium chloride | 0.48 |
| Disodium Edetate | 0.05 |
| Citric acid monohydrate | 0.021 |
| Sodium citrate dihydrate | 0.56 |
| NaOH/HCl | QS to pH 6.5 to 8.0 |
| Purified water | QS |

D. Part II Disinfecting Composition

| Ingredient | Amount % (w/v) |
|---|---|
| Polyquaternium-1 | 0.001 + 10% excess |
| Sodium chloride | 0.48 |
| Boric Acid | 0.225 |
| Sodium Borate | 0.08 |
| Mannitol | 0.64 |
| Pationic 138C | 0.005 |
| Tetronic 1304 | 0.25 |
| Disodium Edetate | 0.05 |
| Citric acid monohydrate | 0.016 |
| Sodium citrate dihydrate | 0.46 |
| Purified water | QS |

These Part II compositions are prepared in a similar way as described in Example 2B.

For the preparation of multi-purpose compositions of the present invention, the Part I and II compositions described in the examples above will be combined, stored and mixed in a single bottle assembly in various quantities. In general, preferred amounts will be:

Part I: 1 g of powder or 1 tablet (about 50 mg) of a solid enzyme composition, or 1 ml of liquid enzyme composition.

Part II: about 120 ml (Similarly 2 g of powder, 2 tablets or 2 ml of liquid may be combined with about 240 ml of Part II.)

The preferred enzyme activity in the final multi-purpose solution will be about 5–25 PAU/ml.

EXAMPLE 6

A preferred multi-purpose composition of the present invention comprises

| Ingredient | Amount % (w/v) |
|---|---|
| Me-trypsin | 25 PAU/mL |
| Sodium borate | 0.012 |
| Calcium Chloride | 0.002 |
| Propylene glycol | 0.41 |
| Polyquaternium-1 | 0.001 |
| Boric acid | 0.6 |
| Sodium chloride | 0.1 |
| AMP-95 | 0.45 |
| MAPDA | 0.0005 |
| Sorbitol | 1.2 |
| Sodium citrate | 0.65 |
| Tetronic 1304 | 0.05 |
| Disodium Edetate | 0.05 |
| NaOH/HCl | To adjust pH 6.5 to 8.0 |
| Purified water | QS |

The composition is prepared by adding 1 mL of the composition of Example 2A to 120 mL of the composition of Example 2B.

The enzyme stability examples below (Examples 7–11) employed the following enzyme assay:

Azocasein Method

The following solutions are used in this assay:

1) Buffer solution: 0.05 M sodium phosphate buffer containing 0.9% sodium chloride, pH 7.6.

2) Substrate solution: 2 mg/ml azocasein in the buffer solution mentioned above.

The assay is initiated by mixing 1 ml of an appropriately diluted (such that the enzyme activity is in the range of standard curve) enzyme composition in phosphate buffer with 2 ml of azocasein substrate solution (2 mg/ml). After incubation at 37° C. for 20 minutes, the mixture is removed from the incubator and 1 ml of trichloroacetic acid to (14% w/v) is added to stop the enzyme reaction. The mixture is vortexed well and allowed to stand at room temperature for 20 minutes. After centrifuging at 2500 rpm (with a Beckman GS-6R Centrifuge) for 15 minutes, the supernatant is filtered with a serum sampler. 2 ml of the clear yellow filtrate is then adjusted to a neutral pH with 2 ml of 0.5 N sodium hydroxide and the absorbance of 440 nm wavelength light is measured with a spectrophotometer. The amount of azocasein hydrolyzed is calculated based on a standard curve of known concentrations of azocasein solution developed under identical conditions. An enzyme activity unit ("AZ U") is defined as that amount of enzyme which hydrolyzes 1 µg of azocasein substrate/minute at 37° C.

EXAMPLE 7

Data demonstrating the superior efficacy of Me-trypsin compositions over analogous compositions containing either trypsin or acetylated trypsin, were ascertained. The enzymes were solubilized in a Part I composition containing 50% (w/v) L-sorbose 1% (w/v) borax ($Na_2B_4O_7 \cdot 10H_2O$), at pH 5.79, except the acetylated trypsin composition was at pH 7.54. The compositions were stored at 45° C. for 240 hours. At various time points, enzyme activity was assayed using the azocasein method. The data are illustrated in Table 1, below:

TABLE 1

Comparison of the Stability of Me-Trypsin Versus Other Trypsin Analogs

| | % Activity Remaining | | | | | |
|---|---|---|---|---|---|---|
| Enzyme | 0 Hr. | 64 Hr. | 96 Hr. | 120 Hr. | 144 Hr. | 240 Hr. |
| Native Trypsin | 100.0 | 62.9 | 56.8 | 53.1 | 49.1 | 41.4 |
| Acetylated Trypsin | 100.0 | 53.1 | 45.1 | 42.2 | 38.5 | 31.0 |
| Methyl-Trypsin | 100.0 | 89.4 | 86.3 | 84.7 | 82.2 | 76.1 |

The data show the superior enzyme stability of Me-trypsin in a Part I composition of the present invention over other trypsin related enzyme compositions.

EXAMPLE 8

The following is an example of the stability of Me-trypsin in a disinfecting composition of the present invention as compared to analogous compositions containing trypsin or pancreatin. The enzymes were solubilized in the Example 5C composition. The compositions were stored at room temperature or 30° C. for up to 42 days. At various time points, enzyme activity was assayed using the azocasein method. The data are illustrated in Table 2, below:

TABLE 2

Comparison of the Stability of Me-Trypsin, Trypsin and Pancreatin in a Disinfecting Composition

| Enzyme | 1 day | 2 days | 5 days | 7 days | 14 days | 21 days | 28 days | 35 days | 42 days |
|---|---|---|---|---|---|---|---|---|---|
| | RT | | | | | | | | |
| | % Activity Remaining | | | | | | | | |
| Methyl Trypsin | 100.9 | 100.8 | 97.9 | 99.4 | 100.0 | 98.5 | 96.6 | 96.5 | 94.0 |

TABLE 2-continued

Comparison of the Stability of Me-Trypsin, Trypsin and Pancreatin in a Disinfecting Composition

| Enzyme | 1 day | 2 days | 5 days | 7 days | 14 days | 21 days | 28 days | 35 days | 42 days |
|---|---|---|---|---|---|---|---|---|---|
| Native Trypsin | 102.5 | 101.5 | 98.5 | 93.6 | 85.7 | 79.6 | 74.4 | 73.8 | 61.3 |
| Pancreatin | 97.6 | 93.5 | 73.8 | 79.9 | 71.0 | 64.3 | 59.0 | — | — |

30° C. % Activity Remaining

| | | | | | | | | | |
|---|---|---|---|---|---|---|---|---|---|
| Methyl Trypsin | 99.7 | 97.8 | 96.1 | 93.5 | 91.8 | 86.7 | 82.7 | 80.0 | 76.3 |
| Native Trypsin | 90.8 | 78.7 | 66.7 | 62.4 | 52.4 | — | — | — | — |
| Pancreatin | 71.4 | 75.9 | 50.5 | 55.2 | 52.5 | — | — | — | — |

*Enzyme concentration: 50 µg/ml for all the enzymes except pancreatin, which was 375 µg/ml.

The data presented in Table 2 demonstrate the superior stability of Me-trypsin in a disinfecting composition of the present invention over analogous compositions containing trypsin or pancreatin.

EXAMPLE 9

The following is an example of the stability of Me-trypsin in a disinfecting composition of the present invention as compared to an analogous composition containing trypsin. The enzymes were solubilized in the Example 5C composition. The two compositions were incubated at 35° C. or 40° C. At the appointed time, aliquots were tested for enzyme activity by the azocasein method. Activity levels were compared with initial levels and expressed as percent remaining activity. The results are presented in Table 3, below:

TABLE 3

Comparison of the Thermal Stability of Me-Trypsin and Trypsin in a Disinfecting Solution % Activity Remaining

| | 35° C. | | | | 40° C. | | |
|---|---|---|---|---|---|---|---|
| Enzymes | 24 hrs | 48 hrs | 72 hrs | 168 hrs | 24 hrs | 114 hrs | 168 hrs |
| Native Trypsin | 69.9 | 55.9 | 48.5 | 37.6 | 42.4 | 19.4 | 17.4 |
| Methylated Trypsin | 97.6 | 96.4 | 91.6 | 87.3 | 88.9 | 75.2 | 67.0 |

*Enzyme concentration: 50 µg/ml.

EXAMPLE 10

Data demonstrating the stability of the Part I Me-trypsin composition of Example 2A, at storage temperatures of room temperature, 40°, 45°, 50° and 55° C. were ascertained. At the appointed time, aliquots were tested for enzyme activity by the azocasein method. Activity levels were compared with initial levels and expressed as percent remaining activity. The results are presented in Table 4, below:

TABLE 4

Stability of Me-Trypsin in the Example 2A Composition

| Temperature | Storage Time (weeks) | Percent Remaining Activity |
|---|---|---|
| 55° C. | 1 | 82.1 |
| | 2 | 75.3 |
| | 4 | 46.5 |
| 50° C. | 1 | 91.8 |
| | 2 | 91.8 |
| | 4 | 82.4 |
| | 6 | 81.3 |
| | 8 | 75.2 |
| | 12 | 71.5 |
| 45° C. | 1 | 100 |
| | 2 | 100 |
| | 4 | 92.7 |
| | 6 | 97.8 |
| | 8 | 100 |
| | 12 | 97.6 |
| 40° C. | 1 | 100 |
| | 2 | 100 |
| | 4 | 93.7 |
| | 6 | 100 |
| | 8 | 100 |
| | 12 | 100 |
| RT | 1 | 100 |
| | 2 | 100 |
| | 4 | 94.1 |
| | 6 | 100 |
| | 8 | 100 |
| | 12 | 100 |

EXAMPLE 11

Data demonstrating the stability of the Me-trypsin multi-purpose composition of Example 6 (1 mL of Example 2A dispersed in 120 mL of Example 2B), in comparison to composition container either trypsin or pancreatin, were ascertained. The trypsin or pancreatin compositions were prepared by dispersing 1.4 mL of Example 3B (wherein Me-trypsin was replaced by either trypsin or pancreatin) in 120 mL of Example 2B. The compositions were incubated at room temperature, 30° and 35° C. At the appointed time, aliquots were tested for enzyme activity by the azocasein method. Activity levels were compared with initial levels and expressed as percent remaining activity. The results are presented in Table 5, below:

TABLE 5

Comparison of the Enzyme Stability of the Example 6 Composition With Other Compositions

| Temperature | Storage Time (weeks) | % Remaining Activity | | |
|---|---|---|---|---|
| | | Me-Trypsin | Trypsin | Pancreatin |
| 35° C. | 1 | 82.1 | 30.8 | 36.1 |
| | 2 | 75.0 | 19.9 | 39.6 |
| | 3 | 71.4 | 13.3 | 30.0 |
| | 4 | 65.2 | 12.8 | 29.8 |
| | 6 | 55.9 | 8.8 | 27.5 |
| | 8 | 50.3 | 5.2 | 25.1 |
| 30° C. | 1 | 97.0 | 65.7 | 59.3 |
| | 2 | 97.2 | 54.6 | 59.9 |
| | 3 | 91.1 | 47.1 | 46.4 |
| | 4 | 90.6 | 44.9 | 51.6 |
| | 6 | 85.8 | 35.8 | 38.4 |
| | 8 | 83.0 | 30.4 | 35.5 |
| RT | 1 | 101.3 | 93.5 | 87.8 |
| | 2 | 99.6 | 86.8 | 85.3 |
| | 3 | 98.4 | 82.5 | 75.5 |

TABLE 5-continued

Comparison of the Enzyme Stability of the Example 6 Composition With Other Compositions

| Temperature | Storage Time (weeks) | % Remaining Activity | | |
|---|---|---|---|---|
| | | Me-Trypsin | Trypsin | Pancreatin |
| | 4 | 98.1 | 79.5 | 81.0 |
| | 6 | 96.0 | 71.0 | 61.5 |
| | 8 | 96.4 | 64.2 | 56.0 |

EXAMPLE 12

The following is an example of the stability of Et-trypsin or Me-trypsin in a disinfecting composition of the present invention as compared to an analogous composition containing trypsin. The enzymes were solubilized in the Example 2B composition. The compositions were stored at 37° or 50° C. for 8 days or 30 hours, respectively. At various time points, enzyme activity was assayed using the azo-casein method. The data are illustrated in Tables 6 and 7, below:

TABLE 6

Comparison of the Stability of Et-Trypsin and Trypsin in a Disinfecting Composition 37° C.
% Activity Remaining

| Enzyme | 1 Hour | 2 Hours | 4 Hours | 6 Hours | 8 Hours | 1 day | 2 days | 4 days | 8 days |
|---|---|---|---|---|---|---|---|---|---|
| Trypsin | 86.8 | 80.0 | 72.7 | 62.9 | 56.6 | 37.6 | 26.8 | 17.9 | 11.2 |
| Et-Trypsin | 100 | 100 | 95.2 | 99.3 | 97.9 | 89.7 | 82.5 | 76.4 | 65.6 |

*Enzyme concentration: 50 μg/ml for all the enzymes except pancreatin, which was 375 μg/ml.

TABLE 7

Comparison of the Stability of Et-Trypsin, Me-Trypsin and Trypsin in a Disinfecting Composition 50° C.
% Activity Remaining

| Enzyme | 0.5 Hour | 1 Hour | 2 Hours | 4 Hours | 6 Hours | 22 Hours | 30 Hours |
|---|---|---|---|---|---|---|---|
| Trypsin | 81.1 | 66.2 | 45.9 | 31.8 | 19.4 | 9.3 | 4.5 |
| Me-Trypsin | 97.7 | 100 | 90.0 | 76.9 | 68.0 | 45.0 | 35.0 |
| Et-Trypsin | 100 | 100 | 93.9 | 79.7 | 69.7 | 43.0 | 40.0 |

*Enzyme concentration: 50 μg/ml for all the enzymes except pancreatin, which was 375 μg/ml.

EXAMPLE 13

The disinfecting efficacy of the cleaning and disinfecting methods of the present invention was evaluated by determining the rate and extent of kill achieved with the multi-purpose solution prepared from the Example 2A and 2B compositions. The multi-purpose solution was tested against *Serratia marcescens, Staphylococcus aureus, Pseudomonas aeruginosa, Candida albicans* and *Fusarium solani*. The test procedures and results are described below.

The following procedure was used:

A 0.1 mL volume of inoculum ($10^8$ colony forming units/mL) was first added to a 10 mL volume of the disinfecting solution of Example 2B, followed by the addition of 2 drops (1 drop equals about 30–40 μL using a "Droptainer") of the liquid enzyme composition of Example 2A. A similarly inoculated 10 mL volume of the disinfecting solution of Example 2B was used as a control. The solutions were maintained at room temperature throughout the test. Each microorganism and test solution was tested individually. Sets of four replicate (n=8) samples were tested for each organism.

At selected time intervals of 1, 2, 3, 4, 6, 24 and 168 hours, a 1 mL volume of the inoculated test solution containing *Serratia marcescens, Staphylococcus aureus, Pseudomonas aeruginosa, Candida albicans* and *Fusarium solani* was removed and appropriate serial dilutions were made in sterile 0.9% sodium chloride solution dilution blanks. Pour-plates were prepared with soybean-casein digest agar containing 0.07% Asolectin and 0.5% Polysorbate 80. At Time 0, a 1.0 mL volume of the saline control was removed and serial dilution pour-plates were prepared using the same recovery medium and dilution blanks. The Time 0 saline control count was used as the initial count. The pour-plates were incubated at 30°–35° C. for appropriate incubation periods. The number of surviving organisms at each time interval was then determined. The test results, expressed as log reductions, are presented in Table 8, below.

TABLE 8

Disinfecting Efficacy of a Multi-Purpose Solution of the Present Invention

| Microorganism | Time (hours) | Log Reduction |
|---|---|---|
| C. albicans | 1 | 0.8 |
| | 2 | 0.9 |
| | 3 | 1.0 |
| | 4 | 1.1 |
| | 6 | 2.6 |
| | 24 | 5.6 |
| | 168 | 6.0* |
| F. solani | 1 | 3.1 |
| | 2 | 3.8 |
| | 3 | 4.3 |
| | 4 | 5.1 |
| | 6 | 5.8* |
| | 24 | 5.8* |
| | 168 | 5.8* |
| P. aeruginosa | 1 | 4.8 |
| | 2 | 4.8 |
| | 3 | 5.3 |
| | 4 | 6.1* |
| | 6 | 6.1* |
| | 24 | 6.1* |
| | 168 | 6.1* |

TABLE 8-continued

Disinfecting Efficacy of a Multi-Purpose Solution of the Present Invention

| Microorganism | Time (hours) | Log Reduction |
|---|---|---|
| S. marcescens | 1 | 2.1 |
| | 2 | 2.6 |
| | 3 | 2.9 |
| | 4 | 3.3 |
| | 6 | 4.5 |
| | 24 | 4.9 |
| | 168 | 6.0* |
| S. aureus | 1 | 2.7 |
| | 2 | 3.0 |
| | 3 | 3.3 |
| | 4 | 3.4 |
| | 6 | 3.8 |
| | 24 | 6.0* |
| | 168 | 6.0* |

*Indicates that no survivors (less than 10 cfu/mL) were recovered

EXAMPLE 14

The following example illustrates the cleaning efficacy of a multi-purpose composition (Example 6) of the present invention. The cleaning efficacy was determined using the following protocol.

1. Physiological/Thermal Combination Model

Each lens was first soaked in a 5 ml lysozyme solution (native or C14-labeled, 1.0 mg/ml in 0.05M phosphate buffer containing 0.9% sodium chloride, pH 7.4) at 37° C. for 24 hours, then removed to a saline solution (2 ml) and heated at 90° C. for 15 minutes.

2. Cleaning and Assessment of Lysozyme Deposits

Each deposited lens was placed in a 5 ml of a test solution and agitated in a rotary shaker at room temperature overnight (usually >12 hours). The compositions tested were: 1) the Example 6 composition (Me-trypsin), 2) 1 drop of Example 3B (except Me-trypsin was replaced by trypsin) in 5 mL of the Example 2B composition and 3) 1 drop of Supraclens® Daily Protein Remover (pancreatin) in 5 mL of the Example 2B composition. After rinsing the lens by dipping three times in three consecutive 40 ml saline solution, the lens was subjected to extraction with 5 ml ACN/TFA solution (acetonitrile/trifluoroacetic acid/water: 500/1/500 v/v) for at least 2 hours. No mechanical rubbing was applied to the cleaning regimen. Both the extract and the soaking solution were then assessed for lysozyme by the protein intrinsic fluorescence method using a fluorescence spectrophotometer (excitation wavelength is 280 nm, emission wavelength is 354 nm), or by a scintillation counter for the C14-lysozyme. The quantification of lysozyme was based on a lysozyme standard curve established using the same vehicle and instrumental setting used for the lens extract and lens soaking solution. The results are show in Tables 9–10.

TABLE 9

Cleaning Efficacy Using the Fluorescence Method

| | Lysozyme ($\mu$g/Lens) | | | |
|---|---|---|---|---|
| Enzyme | Hydrolysate | ACN/TFA Extract | Total | % Cleaning Efficacy |
| SupraClens ® | 146.35 | 43.76 | 190.10 | 77.0 |
| Trypsin | 233.45 | 83.92 | 317.40 | 73.6 |
| Methylated Trypsin | 201.45 | 72.90 | 274.35 | 73.4 |

TABLE 10

Cleaning Efficacy Using the C-14 Method

| | Lysozyme ($\mu$g/Lens) | | | | |
|---|---|---|---|---|---|
| Enzyme | Hydrolysate | ACN/TFA Extract | Lens | Total | % Cleaning Efficacy |
| SupraClens ® | 98.69 | 38.5 | 4.74 | 141.93 | 69.5 |
| Trypsin | 145.02 | 48.43 | 3.57 | 197.02 | 73.6 |
| Methylated Trypsin | 141.61 | 52.85 | 3.75 | 198.21 | 71.4 |

The invention in its broader aspects is not limited to the specific details shown and described above. Departures may be made from such details within the scope of the accompanying claims without departing from the principles of the invention and without sacrificing its advantages.

What is claimed is:

1. A stable, concentrated liquid enzyme composition for cleaning a contact lens comprising an alkyl trypsin in an amount effective to clean the lens and a liquid vehicle.

2. A composition according to claim 1, wherein the suitable liquid vehicle comprises from 10–90% w/v of a water-miscible organic molecule and water.

3. A composition according to claim 2, wherein the water-miscible organic molecule is a polyol.

4. A composition according to claim 3, wherein the polyol is selected from the group consisting of glycerol, 1,2-propane diol, 1,3-propane diol, and ethylene glycol.

5. A composition according to claim 2, wherein the composition further comprises a borate/boric acid compound in an amount effective to enhance the stability of the alkyl trypsin.

6. A composition according to claim 5, wherein the composition further comprises calcium ion in an amount effective to enhance the stability of the alkyl trypsin.

7. A composition according to claim 4, wherein the composition further comprises a borate/boric acid compound calcium ion in amounts effective to enhance the stability of the alkyl trypsin.

8. A composition according to claim 7, wherein the composition comprises an alkyl trypsin in an amount effective to clean the lens, propylene glycol or glycerol in the amount of from 40–85% w/v, a borate/boric acid compound in the amount of from 0.5–2.0% w/v and a calcium ion concentration of from 10 to 45 millimolar.

9. A composition according to claim 7, wherein the alkyl trypsin is selected from the group consisting of methyl trypsin and ethyl trypsin.

10. A composition according to claim 9, wherein the composition comprises methyl trypsin, 50% w/v propylene glycol, 1.5% w/v sodium borate, 0.25% w/v calcium chloride and water.

11. A composition according to claim 9, wherein the composition comprises methyl trypsin, 50% w/v glycerol, 1.5% w/v sodium borate, 0.25% w/v calcium chloride and water.

12. A composition according to claim 9, wherein the composition comprises methyl trypsin, 50% w/v PEG-400, 25% w/v glycerol, 1.5% w/v sodium borate, 0.25% w/v calcium chloride and water.

13. A method of cleaning a contact lens which comprises:
    forming an aqueous enzymatic cleaning solution by dispersing a small amount of a concentrated liquid enzyme cleaning composition in an aqueous solvent, said cleaning composition comprising an alkyl trypsin in an amount effective to clean the lens and a liquid vehicle; and soaking the lens in the enzymatic cleaning solution for a period of time sufficient to clean the lens.

14. A method according to claim 13, wherein the suitable liquid vehicle comprises from 10–90% of a water-miscible organic molecule and water.

15. A method according to claim 13, wherein the water-miscible organic molecule is a polyol.

16. A method according to claim 15, wherein the polyol is selected from the group consisting of glycerol, 1,2-propane diol, 1,3-propane diol, and ethylene glycol.

17. A method according to claim 16, wherein the liquid enzyme cleaning composition further comprises an effective amount of a borate/boric acid compound.

18. A method according to claim 17, wherein the liquid enzyme cleaning composition further comprises an effective amount of calcium ion.

19. A method according to claim 16, wherein the liquid enzyme cleaning composition further comprises an effective amount of a borate/boric acid compound and an effective amount of calcium ion.

20. A method according to claim 19, wherein the liquid enzyme cleaning composition comprises an alkyl trypsin in an amount effective to clean the lens, propylene glycol or glycerol in the amount of from 40–70% w/v, a borate/boric acid compound in the amount of from 0.5–2.0% w/v and a calcium ion concentration of from 10 to 45 millimolar.

21. A method according to claim 19, wherein alkyl trypsin is selected from the group consisting of methyl trypsin and ethyl trypsin.

22. A method according to claim 21, wherein the liquid enzyme cleaning composition comprises methyl trypsin, 50% w/v propylene glycol, 1.5% w/v sodium borate, 0.25% w/v calcium chloride and water.

23. A method according to claim 21, wherein the liquid enzyme cleaning composition comprises methyl trypsin, 50% w/v glycerol, 1.5% w/v sodium borate, 0.25% w/v calcium chloride and water.

24. A method according to claim 21, wherein the liquid enzyme cleaning composition comprises methyl trypsin, 50% w/v PEG-400, 25% w/v glycerol, 1.5% w/v sodium borate, 0.25% w/v calcium chloride and water.

* * * * *